US008790366B2

(12) United States Patent
Cordova

(10) Patent No.: US 8,790,366 B2
(45) Date of Patent: Jul. 29, 2014

(54) FAN-SHAPED CANNULA FOR SEALING OPHTHALMIC INCISIONS

(75) Inventor: Diana M. Cordova, Duncanville, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 1756 days.

(21) Appl. No.: 11/939,005

(22) Filed: Nov. 13, 2007

(65) Prior Publication Data
US 2009/0125057 A1 May 14, 2009

(51) Int. Cl.
*A61B 17/03* (2006.01)

(52) U.S. Cl.
USPC ............. 606/214; 128/203.15; 128/203.12; 156/69; 222/129; 222/153.07; 222/490

(58) Field of Classification Search
USPC ............... 606/213–214; 604/87, 240, 244; 128/203.15, 203.21; 222/81–85, 190, 222/129, 153.07, 490; 156/69
See application file for complete search history.

(56) References Cited

U.S. PATENT DOCUMENTS

| | | | | |
|---|---|---|---|---|
| 1,557,620 A * | 10/1925 | Robinson | .................. | 604/301 |
| 2,330,695 A * | 9/1943 | Eweson | .................. | 604/301 |
| 2,623,663 A * | 12/1952 | Gassaway | .................. | 222/490 |
| 2,919,696 A * | 1/1960 | Rinaldy | .................. | 294/1.2 |
| 3,250,436 A * | 5/1966 | Kurtz | .................. | 222/153.07 |
| 3,342,318 A * | 9/1967 | Ruekberg et al. | .................. | 206/540 |
| 3,524,537 A * | 8/1970 | Winter | .................. | 206/229 |
| 3,653,380 A * | 4/1972 | Hansen | .................. | 128/203.15 |
| 3,964,643 A * | 6/1976 | Morane et al. | .................. | 222/129 |
| 3,998,226 A * | 12/1976 | Harris | .................. | 128/203.15 |
| 4,138,040 A * | 2/1979 | Stock | .................. | 222/420 |
| 4,530,356 A | 7/1985 | Helfgott et al. | | |
| 4,595,434 A * | 6/1986 | Eckstein et al. | .................. | 156/69 |
| 4,941,872 A * | 7/1990 | Felix et al. | .................. | 604/27 |
| 5,046,493 A * | 9/1991 | Kropkowski et al. | .................. | 128/203.15 |
| 5,106,221 A * | 4/1992 | Diot et al. | .................. | 401/132 |
| 5,112,339 A | 5/1992 | Zelman | | |
| 5,215,221 A * | 6/1993 | Dirksing | .................. | 222/94 |
| 5,254,084 A * | 10/1993 | Geary | .................. | 604/29 |
| 5,292,332 A * | 3/1994 | Lee | .................. | 606/213 |
| 5,336,170 A * | 8/1994 | Salerno et al. | .................. | 604/24 |
| 5,407,441 A | 4/1995 | Greenbaum | | |
| 5,409,125 A * | 4/1995 | Kimber et al. | .................. | 215/48 |
| 5,571,246 A * | 11/1996 | Alldredge | .................. | 128/200.23 |
| 5,649,943 A | 7/1997 | Amoils | | |
| 5,665,106 A * | 9/1997 | Hammerslag | .................. | 606/214 |

(Continued)

OTHER PUBLICATIONS

Katena Products, Inc., Katena Eye Instruments Catalog, downloaded on Nov. 17, 2006, 1 page, http://www.katena.com/html/product_detail.cfm.

*Primary Examiner* — Vy Q Bui

(57) ABSTRACT

A device for delivering an incision sealant includes a housing, a seal, and a cannula. The housing at least partially encloses a chamber that holds a quantity of a sealant. The seal is located on one end of the housing and contains the sealant in the chamber. Likewise, a similar seal may be located at the tip end of the fan-shaped cannula. The cannula is fluidly coupled to the chamber, is disposed along an axis, and has a generally fan-shaped end. The generally fan-shaped end has a top surface and an opening for dispensing the sealant. The shape of the generally fan-shaped end is configured to apply sealant to an incision geometry or to conform to the geometry of an eye.

18 Claims, 5 Drawing Sheets

(56) References Cited

U.S. PATENT DOCUMENTS

| | | | |
|---|---|---|---|
| 5,730,336 A * | 3/1998 | Lerner | 222/490 |
| 5,730,748 A * | 3/1998 | Fogarty et al. | 606/159 |
| 5,735,833 A * | 4/1998 | Olson | 604/289 |
| 5,752,964 A | 5/1998 | Mericle | |
| 5,928,611 A * | 7/1999 | Leung | 422/131 |
| 6,027,471 A * | 2/2000 | Fallon et al. | 604/59 |
| 6,085,742 A * | 7/2000 | Wachter et al. | 128/200.23 |
| 6,135,984 A | 10/2000 | Dishler | |
| 6,398,277 B1 * | 6/2002 | McDonald | 294/1.2 |
| 6,413,245 B1 | 7/2002 | Yaacobi et al. | |
| 6,425,704 B2 * | 7/2002 | Voiers et al. | 401/196 |
| 6,530,374 B1 * | 3/2003 | Ferraro | 128/206.29 |
| 6,585,689 B1 * | 7/2003 | Macoviak et al. | 604/103.07 |
| 6,722,364 B2 * | 4/2004 | Connelly et al. | 128/203.15 |
| 6,764,463 B1 * | 7/2004 | Farris | 604/82 |
| 6,782,887 B2 * | 8/2004 | Sullivan | 128/203.15 |
| 6,845,772 B2 * | 1/2005 | Braithwaite et al. | 128/203.15 |
| 7,040,316 B2 * | 5/2006 | Connelly et al. | 128/203.15 |
| 7,141,048 B1 | 11/2006 | Charles | |
| 7,270,127 B2 * | 9/2007 | Lockhart et al. | 128/203.15 |
| 7,285,107 B1 | 10/2007 | Charles | |
| 7,540,285 B2 * | 6/2009 | Connelly et al. | 128/203.15 |
| 2003/0047184 A1 * | 3/2003 | Lockhart et al. | 128/203.21 |

\* cited by examiner

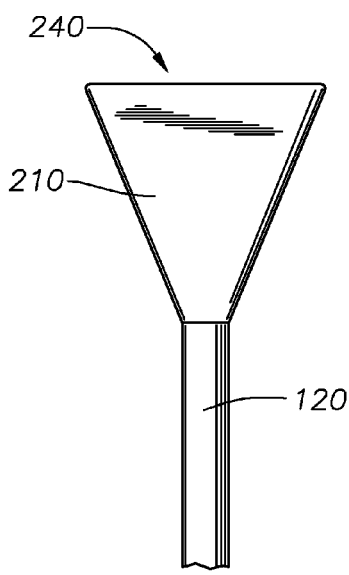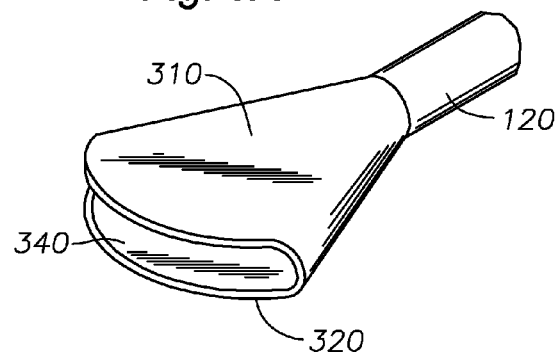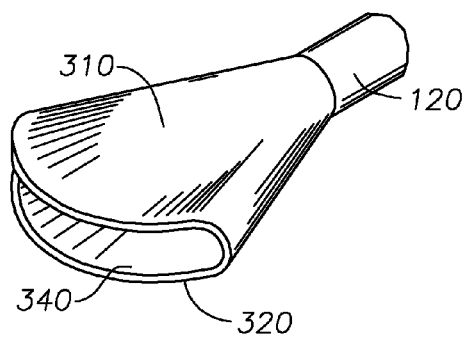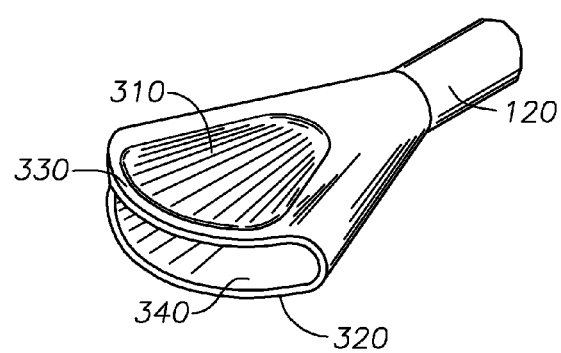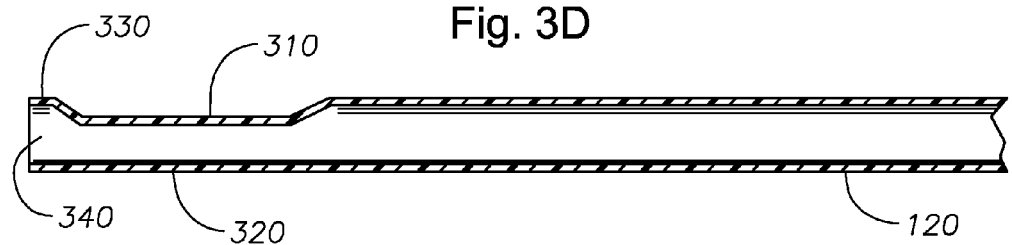

FAN-SHAPED CANNULA FOR SEALING OPHTHALMIC INCISIONS

BACKGROUND OF THE INVENTION

The present invention relates to a device for administering a wound sealant and more particularly to a fan-shaped pre-loaded cannula attached to a syringe device for administering a wound sealant directly to an incision site on the eye.

Anatomically, the eye is divided into two distinct parts—the anterior segment and the posterior segment. The anterior segment extends from the outermost layer of the cornea (the corneal epithelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. Ocular surgery involves making an incision to gain entry to the eye. Various surgical procedures are commonly performed on the anterior and posterior segments of the eye. In the anterior segment, cataract surgery is most common. In the posterior segment, a number of vitreo-retinal procedures are most common.

The eye's natural lens is composed of an outer lens capsule enclosing a lens cortex. Since the human eye functions to provide vision by transmitting light through a clear outer portion called the cornea, and focusing the image by way of a clear crystalline lens onto a retina, the quality of the focused image depends on many factors including the transparency of the lens. When age or disease causes the lens to become less transparent, vision deteriorates because of the diminished light which can be transmitted to the retina. This deficiency in the lens of the eye is medically known as a cataract. An accepted treatment for this condition is cataract surgery which involves the removal and replacement of the lens cortex by an artificial intraocular lens (IOL).

In the United States, the majority of cataractous lenses are removed by a surgical technique called phacoemulsification. During this procedure, an incision of a few millimeters in size is made in the cornea or sclera. By way of the incision, a thin phacoemulsification cutting tip is inserted into the diseased lens and vibrated ultrasonically. The vibrating cutting tip liquefies or emulsifies the lens cortex material so that it may be aspirated out of the eye. The diseased lens material, once removed, is replaced by an IOL.

The IOL is injected into the eye through the same small incision used to remove the diseased lens cellular material. The IOL is placed in an IOL injector in a folded state to avoid enlarging the incision. The tip of the IOL injector is inserted into the incision, and the lens is delivered into the lens capsular bag.

Vitreo-retinal procedures include a variety of surgical procedures performed on the posterior segment of the eye to restore, preserve, and enhance vision. A vitrectomy is a common part of a vitreo-retinal procedure. A vitrectomy, or surgical removal of the vitreous body, may be performed to clear blood and debris from the eye, to remove scar tissue, or to alleviate traction on the retina. The vitreous body is also removed if it is pulling or tugging the retina from its normal position. Some of the most common eye conditions that require a vitrectomy include complications from diabetic retinopathy such as retinal detachment or bleeding, macular hole, retinal detachment, pre-retinal membrane fibrosis, bleeding inside the eye (vitreous hemorrhage), injury or infection, and certain problems related to previous eye surgery.

A surgeon performs a vitrectomy with a microscope and special lenses designed to provide a clear image of the posterior segment. Several tiny incisions are made on the sclera at the pars plana. The surgeon inserts microsurgical instruments through the incisions, such as a fiber optic light source to illuminate inside the eye, an infusion line to maintain the eye's shape during surgery, and instruments to cut and remove the vitreous body.

During each of these ophthalmic procedures, one or more tiny incisions are made to gain access to the various eye structures. These incisions are typically made with custom knives that produce a specific wound geometry. The wound geometry allows access for various surgical instruments. At the conclusion of the procedure, it may be necessary to close the incisions. Because the eye is very sensitive to traditional forms of wound closure, like sutures, various wound sealant compounds may be advantageously used. Some sealants are applied as one part and others are composed of two or more parts that must mix simultaneously to form a seal. For ocular incisions, the quantities of sealant required can be very small, on the order of a few microliters. Formation of a strong seal can require complete coverage of the incision in a single application. Applying these compounds can be difficult because of the location and geometry of the wound, and because of the anatomy of the eye.

For example, a blade may be coated with a sealant and placed inside an incision. However, this process requires proper placement of the sealant on the blade and care in its application. With a blade smaller than the incision, a stroking motion (in-and-out and/or side-to-side) would be required to coat the entire surface of the incision. The brief presence of the blade in between the inner surfaces of the incision can hinder the formation of a strong adhesive seal with complete coverage. Distortion of the incision by insertion of a blade or simple cannula can cause gaping and leakage of intraocular fluids which interferes with strong seal formation.

Effective sealant use in the eye requires a different device and method than for other applications. Accordingly, it would be desirable to have a specially designed fan-shaped pre-loaded cannula attached to a syringe device for injecting small quantities of wound sealant simultaneously and with complete coverage to the entire incision site on the eye with minimal gaping.

SUMMARY OF THE INVENTION

In one embodiment consistent with the principles of the present invention, the present invention is a device for delivering an incision sealant. The device includes a housing with an attached cannula. The housing at least partially encloses a chamber that can be filled with a quantity of a sealant from a pre-loaded syringe. The cannula is fluidly coupled to the chamber, is disposed along an axis, and has a generally fan-shaped end. The generally fan-shaped end has a top and bottom surface and an opening for dispensing the sealant along the entire width of the incision opening simultaneously and with complete coverage in a single application. The shape of the generally fan-shaped end is configured to apply sealant to an incision geometry.

In another embodiment consistent with the principles of the present invention, the present invention is a pre-loaded device for delivering an incision sealant. The device includes a housing with an attached cannula, a seal at the top of the housing, and a seal at the tip of the cannula. The housing at least partially encloses a chamber that holds a quantity of a sealant. The seals are located on the end of the housing and cannula tip and contain the sealant in the chamber. The cannula is fluidly coupled to the chamber, is disposed along an axis, and has a generally fan-shaped end. The generally fan-shaped end has a top and bottom surface and an opening for dispensing the sealant along the entire width of the incision opening simultaneously and with complete coverage in a single application. The shape of the generally fan-shaped end is configured to apply sealant to an incision geometry.

In another embodiment consistent with the principles of the present invention, the present invention is a pre-loaded device for delivering an incision sealant. The device includes a housing with an attached cannula, a seal at the top of the housing, and a seal at the tip of the cannula. The housing at least partially encloses a first chamber and a second chamber. The first chamber holds a quantity of a first part of a sealant, and the second chamber holds a quantity of a second part of the sealant. The seals are located on the end of the housing and cannula tip and contains the first part of the sealant in the first chamber and the second part of the sealant in the second chamber. The cannula is fluidly coupled to the chamber, is disposed along an axis, and has a generally fan-shaped end. The generally fan-shaped end has a top and bottom surface and an opening for dispensing the sealant along the entire width of the incision opening simultaneously and with complete coverage in a single application. The shape of the generally fan-shaped end is configured to apply sealant to an incision geometry.

In another embodiment consistent with the principles of the present invention, the present invention is a method of applying a sealant to an ophthalmic incision. The method includes connecting a fan-shaped cannula to a syringe that is pre-loaded with sealant. The syringe plunger is slightly depressed to extrude sealant and remove void volume. The device tip is inserted in the incision and the syringe plunger depressed to expel a flow of sealant along the width of the incision opening with complete coverage in a single application.

In another embodiment consistent with the principles of the present invention, the present invention is a method of applying a sealant to an ophthalmic incision. The method includes connecting a fan-shaped cannula that is pre-loaded with sealant to an empty syringe. The syringe plunger is depressed to break the frangible seal on the housing and the cannula tip. After the sealant appears at the opening, the device tip is inserted in the incision and the syringe plunger depressed to expel sealant along the incision opening with complete coverage in a single application. Pneumatic power may be used to move the syringe plunger.

In another embodiment consistent with the principles of the present invention, the present invention is a method of applying a sealant to an ophthalmic incision. The method includes removing a seal by removing a sealing strip or by breaking a sealing tab along a score line portion of a fan-shaped cannula. Various score lines can be present along the cannula to allow the surgeon to select the tip width best matching the incision width. Various score lines could also indicate the location of a different opening geometry such as oval or oblong. By engaging a plunger, the housing seal is broken and pressure is applied to the chamber containing a quantity of a sealant. The tip end of the fan-shaped cannula is inserted into an incision and the sealant is expelled along the entire width of the incision opening with complete coverage in a single application. Any excess sealant can be removed by moving the edge of the fan-shaped cannula across the outer surface of the eye and the incision.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2D is a top side view of the fan-shaped cannulas whose tips are pictured in FIGS. 2A-2C.

FIGS. 3A-3C are perspective views of the tip end of three fan-shaped cannulas according to the principles of the present invention.

FIG. 3D is a cross section view of the fan-shaped cannula of FIG. 3C.

DETAILED DESCRIPTION OF THE PREFERRED EMBODIMENTS

Reference is now made in detail to the exemplary embodiments of the invention, examples of which are illustrated in the accompanying drawings. Wherever possible, the same reference numbers are used throughout the drawings to refer to the same or like parts.

Figure 1:
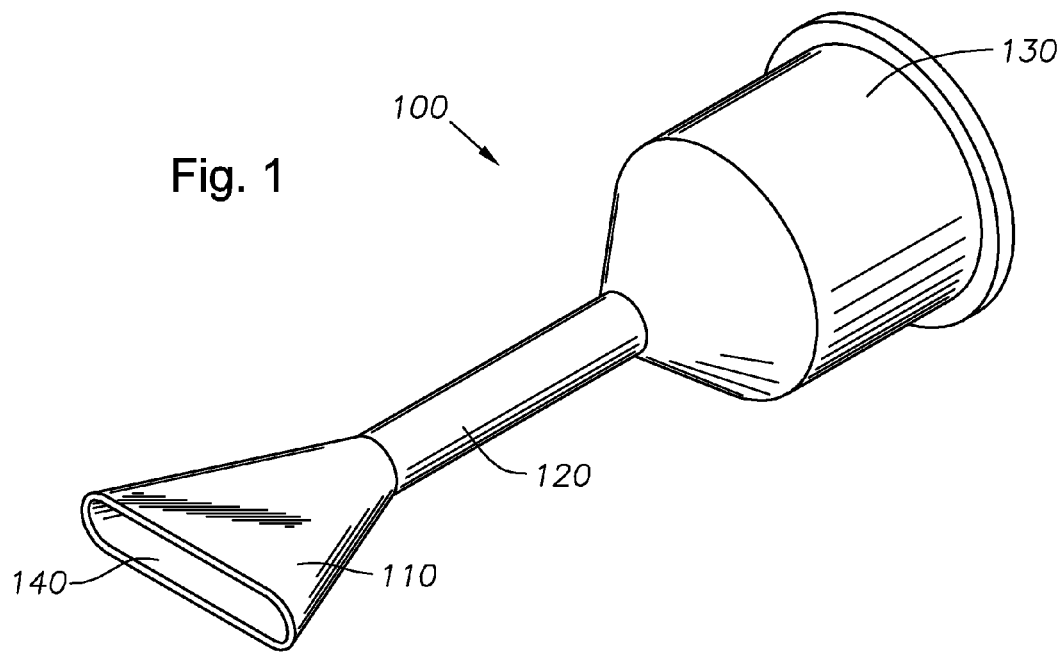
FIG. 1 is a perspective view of a fan-shaped cannula incision sealing device according to the principles of the present invention.

FIG. 1 is a perspective view of a fan-shaped cannula incision sealing device according to the principles of the present invention. In FIG. 1, device 100 includes a fan-shaped tip 110, a cannula 120, a chamber 130 and a tip opening 140. Chamber 130 holds a quantity of a sealant for sealing an incision. In this application, the term "sealant" includes adhesives, glues, two-part epoxies, and like materials for adhering the edges of an incision or wound.

Cannula 120 carries the sealant to the fan-shaped tip 110 where it is dispensed through the tip opening 140. Fan-shaped tip 110 is configured to fit into the incision and properly deliver a quantity of sealant. Preferably, fan-shaped tip 110 has an oblong tip opening 140 as shown. This shape allows fan-shaped tip 110 to fill the incision opening. In other words, the shape of fan-shaped tip is such that it generally contacts the entire perimeter of the incision surface. Such a configuration minimizes gapping during use and allows for a more precise delivery of sealant. In such a case, there is little or no gap between fan-shaped tip 110 and the incision. Tip opening 140 may also be oval or rectangular in shape to facilitate dispensing of the sealant.

Cannula 120 is generally hollow and can be of any configuration. Cannula 120 and fan-shaped tip 110 are typically formed as a single piece. Chamber 130 can be of any suitable configuration and holds a sealant. Fan-shaped tip 110 and cannula 120 are preferably made of a polymer such as polyethylene or polypropylene. In such a case, they can be manufactured using a blow molding technique. In another embodiment of the present invention, chamber 130 is integral with cannula 120 and fan-shaped tip 110.

Various liquid sealants dispensed by device 100 can be used to seal cataract surgery incisions. Typical cataract incisions include clear corneal incisions or sclero-corneal incisions of the tunnel-type or beveled-type. These incisions are typically small—on the order of a few millimeters or less. In order for sealants to be most efficaciously used, the entire edge of the incision should be rapidly and simultaneously coated with sealant to obtain complete coverage in a single application. It is also desirable to provide some coating inside the incision tunnel as well.

As such, fan-shaped tip opening 140 is oblong and wide enough to cover the entire width of the incision. Fan-shaped tip 110 is also tapered to minimize gapping during insertion into the incision. Fan-shaped tip 110 is inserted into an incision or placed on the surface of an incision. A sealant is rapidly expelled from fan-shaped tip opening 140 to cover the incision. In one mode of operation, fan-shaped tip is placed inside the incision and the sealant coats the interior of the incision. In another mode, the fan-shaped tip is placed on top of the incision, and the edges of the incision are coated with sealant.

Figure 2A:
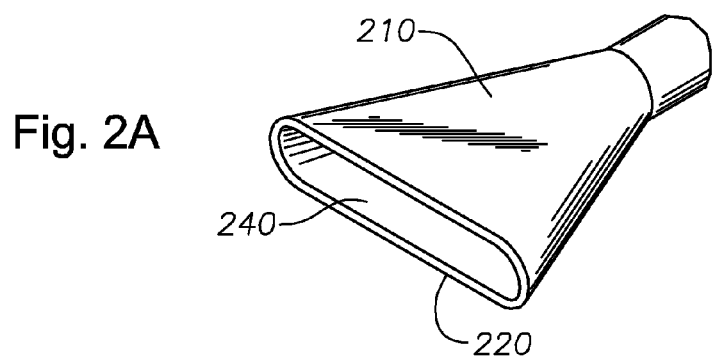
FIGS. 2A-2C are perspective views of the tip end of three fan-shaped cannulas according to an embodiment of the present invention.
Figure 2B:
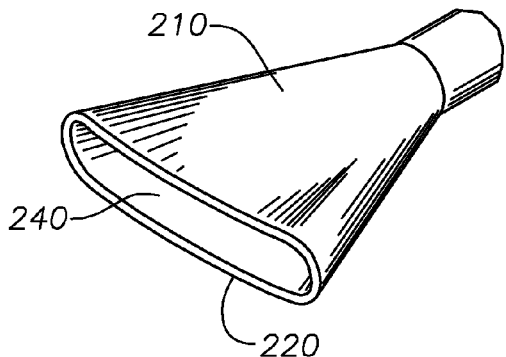
Figure 2C:
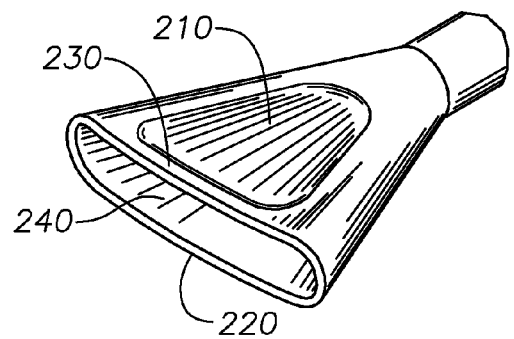

FIGS. 2A-2C are perspective views of the tip end of three fan-shaped cannulas (straight tip 2A, curved tip 2B, spoon tip 2C) according to an embodiment of the present invention. The shape of the cannula tip can be described with reference to two perpendicular planes that intersect at tip opening 240. The cannula axis lies in the first plane such that it bisects tip opening 240. The second plane is perpendicular to the first plane and contains tip opening 240. The straight fan-shaped tip flares-out from the cannula into a fan-shape in the first plane and in the second plane (perpendicular to the first plane) is tapered toward tip opening 240. Tip opening 240 can be oval or oblong. For the straight tip of FIG. 2A, the edges of the tip opening 240 are straight from corner to corner. For the curved tip of FIG. 2B, tip opening 240 lies in a plane and its top and bottom edges are curved as shown. For the spoon tip of FIG. 2C, tip opening 240 lies in a plane and its top and bottom edges are curved as shown. In addition, a depression is located on surface 210 to form a spoon-type shape.

Each of these three fan-shaped cannulas are designed to deliver a quantity of sealant to fit the geometry of a small incision. FIG. 2A shows a generally oblong or oval shaped tip end. Top and bottom surfaces (210, 220) of the tip are generally flat. In FIG. 2B, the surfaces (210, 220) and the tip opening are generally curved. The opening of the tip is generally oblong with a curve. This curve can be symmetric as shown (with the curve on the top end of the opening and the bottom end of the opening being generally similar). The curve may also be asymmetric to fit a particular incision geometry. In FIG. 2C, top surface 210 is generally concave and bottom surface 220 is generally convex. As such, the tip is spoon-shaped with the top surface 210 forming a spoon-like depression. A lip 230 is formed above the tip opening 240. In some cases, lip 230 assists in the proper placement of sealant in or on an incision. Lip 230 can act as a scraper to remove any excess sealant. The edges depicted in FIGS. 2A and 2B can also act to scrape away any excess sealant.

FIG. 2D is a top side view of the fan-shaped cannulas whose tips are pictured in FIGS. 2A-2C. In FIG. 2D, opening 240 is located at the top end of the drawing. A surface 210 with a fan-shaped profile and tapered tip opening is also depicted. The fan-shaped profile extends from cannula 120 to tip opening 240. In this embodiment, tip opening 240 lies generally in a plane perpendicular to the plane of the paper as shown.

Figure 3E:
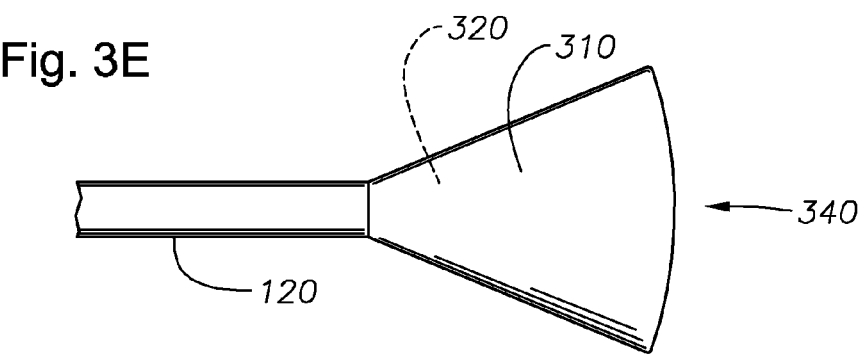
FIG. 3E is a side view of the cannulas of FIGS. 3A-3C.

FIGS. 3A-3C depict three fan-shaped cannulas similar to those depicted in FIGS. 2A-2C. However, the fan-shaped cannulas of FIGS. 3A-3C also include a curved profile along the edge of tip opening 340. This curved profile is depicted in FIG. 3E. In these embodiments, the tip opening 340 lies along a curvilinear surface, such as the curved surface of a cylinder. In this manner, the middle part of the tip opening 340 extends beyond the ends of the tip opening 340. While depicted as being curved outward from the fan-shaped end, the tip opening 340 of the present invention may also be curved inward so that the ends of the tip opening 340 extend beyond the middle of the tip opening 340. Such curved profiles may be adapted to fit an incision geometry or conform to the generally spherical shape of the eye.

FIG. 3A depicts a fan-shaped cannula with a curved tip opening 340. Top and bottom surfaces 310 and 320, respectively, are generally flat. In this manner, the fan-shaped cannula of FIG. 3A is similar to that of FIG. 2A. However, tip opening 340 has a curved profile as shown in FIG. 3E. The fan-shaped tip extends from cannula 120 to tip opening 340.

FIG. 3B depicts a fan-shaped cannula with a curved tip opening 340 and curved top and bottom surfaces. Top and bottom surfaces 310 and 320, respectively, are generally curved. In this manner, the fan-shaped cannula of FIG. 3B is similar to that of FIG. 2B. However, tip opening 340 has a curved profile as shown in FIG. 3E. The fan-shaped tip extends from cannula 120 to tip opening 340.

FIG. 3C depicts a fan-shaped cannula with a curved tip opening 340 and generally curved top and bottom surfaces that form a spoon shaped cannula tip. Top surface 310 is generally concave, and bottom surface 320 is generally convex so that a lip 330 is formed. In this manner, the fan-shaped cannula of FIG. 3C is similar to that of FIG. 2C. However, tip opening 340 has a curved profile as shown in FIG. 3E. The fan-shaped tip extends from cannula 120 to tip opening 340.

FIG. 3D is a side cross section view of the cannula of FIG. 3C. As shown, top surface 310 has a recess that results in lip 330 at the top end of tip opening 340. Bottom surface does not have such a recess.

Figure 4:
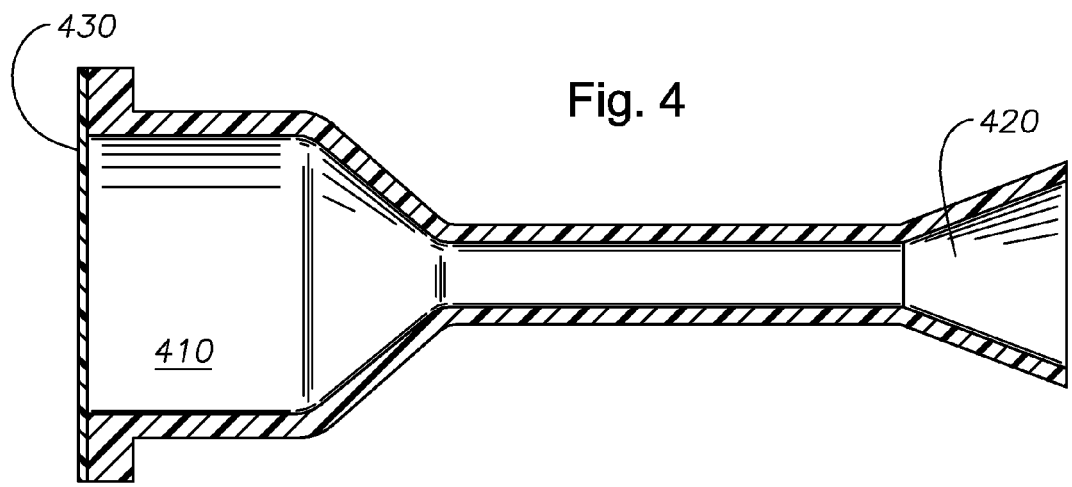
FIG. 4 is a cross section view of a fan-shaped cannula incision sealing device according to the principles of the present invention.

FIG. 4 is a cross-section view of a fan-shaped cannula incision sealing device with a straight tip according to the principles of the present invention. The embodiment of FIG. 4 includes a chamber 410 for holding a quantity of a sealant, fan-shaped cannula 420 for delivering the sealant, and a housing seal 430. Seal 430 retains sealant in chamber 410 and provides an air-tight seal. Likewise, a similar seal may be located at the tip end of fan-shaped cannula 420. Seal 430 may be made of any suitable material. In one embodiment, seal 430 is made of a polymer that can be pierced by a syringe or air pulse. Chamber 410 can be of any suitable configuration and size. Typically, chamber 410 holds enough sealant to properly close an incision. While a straight tip is depicted, any of the previously described tips may be employed.

Figure 5:
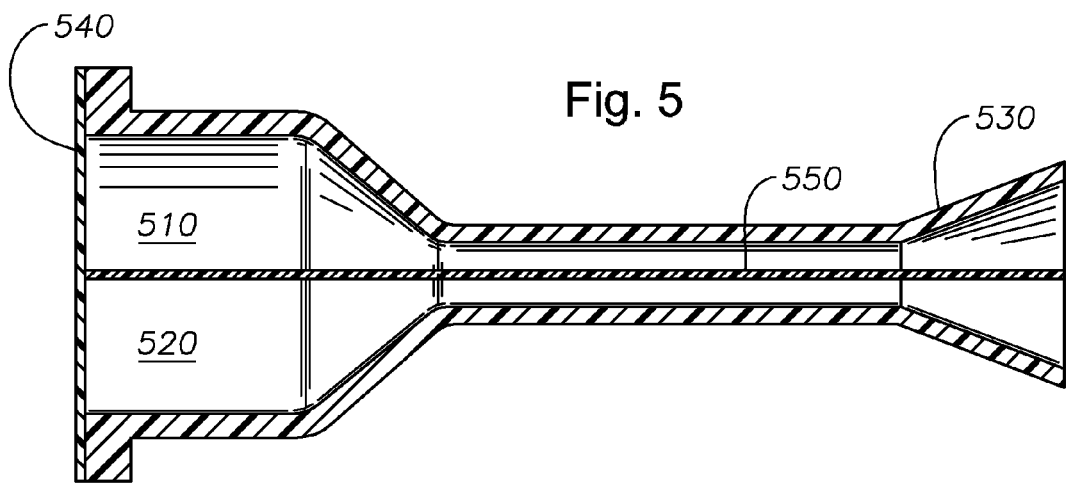
FIG. 5 is a cross section view of a fan-shaped cannula incision sealing device according to the principles of the present invention.

FIG. 5 is a cross-section view of a fan-shaped cannula incision sealing device with a straight tip according to the principles of the present invention. The embodiment of FIG. 5 includes a dual chamber arrangement. First chamber 510 and second chamber 520 are separated by divider 550. Otherwise, fan-shaped cannula 530 and seal 540 are similar to their like components of FIG. 4. The dual chamber arrangement allows for the use of a two part sealant or epoxy. Such a sealant is mixed together when applied to an incision. The mixing of the two part sealant causes a chemical reaction that results in a bonding effect. First chamber 510 and second chamber 520 may be of any suitable shape and size. While depicted as being the same size, one of the chambers may be bigger than the other. Divider 550 is typically a polymer sheet that is inserted or molded into the device. Likewise, a similar seal 560 may be located at the tip end of fan-shaped cannula 540. While a straight tip is depicted, any of the previously described tips may be employed.

Figure 6:
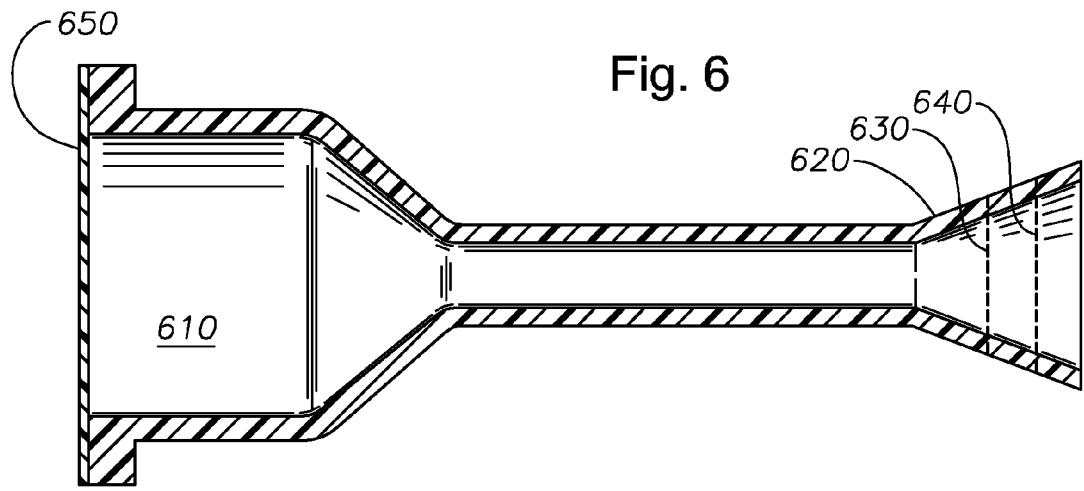
FIG. 6 is a cross section view of a fan-shaped cannula incision sealing device according to the principles of the present invention.

FIG. 6 is a cross-section view of a fan-shaped cannula incision sealing device with a straight tip according to the principles of the present invention. In the embodiment of FIG. 6, the length of fan-shaped cannula 620 and the width of its tip end can be adjusted. Fan-shaped cannula 620 can be snapped or cut along score marks 630 or 640 to be adjusted. In this manner, a single cannula design can be adjusted by the end user to fit various incision configurations. For example, a larger incision may not require any adjustment. A smaller incision may require the end user to snap or cut fan-shaped cannula 620 along score marks 630. This results in a shorter fan-shaped cannula 620 with a smaller opening at its tip end. While a straight tip is depicted, any of the previously described tips may be employed.

In addition, the cross section shape of the fan-shaped cannula 620 may differ along its length so that snapping or cutting it at score marks 630 or 640 results in different shaped openings at its tip end. For example, it may be desirable to have a different shaped opening for a larger incision than for a smaller incision. In such a case, the tip end of fan-shaped cannula 620 may be oblong. When cut or snapped at score marks 630, the opening of the tip end of fan-shaped cannula 620 may be oval. Other shapes or configurations of the opening of tip end are also possible. Chamber 610 and seal 650 are like their similar components in FIG. 4. While depicted as score marks, any other type of cutting guide may be used. For example, a depression or marked line may be used as score marks.

In one mode of operation the device of FIG. 6 can be used to apply a sealant to an ophthalmic incision. A medical professional removes a portion of a fan-shaped cannula along a set of score marks, such as score marks 630 or 640. The device of FIG. 6 is then attached to a plunger. The plunger is located such that it can expel the sealant from the chamber 610. The end of the fan-shaped cannula 620 is inserted into the incision and the plunger is activated to expel the sealant so that the sealant contacts an edge of the incision. Excess sealant is removed by applying an edge of the fan-shaped cannula 620 to the incision. This edge acts as a scraper to remove excess sealant.

Figure 7:
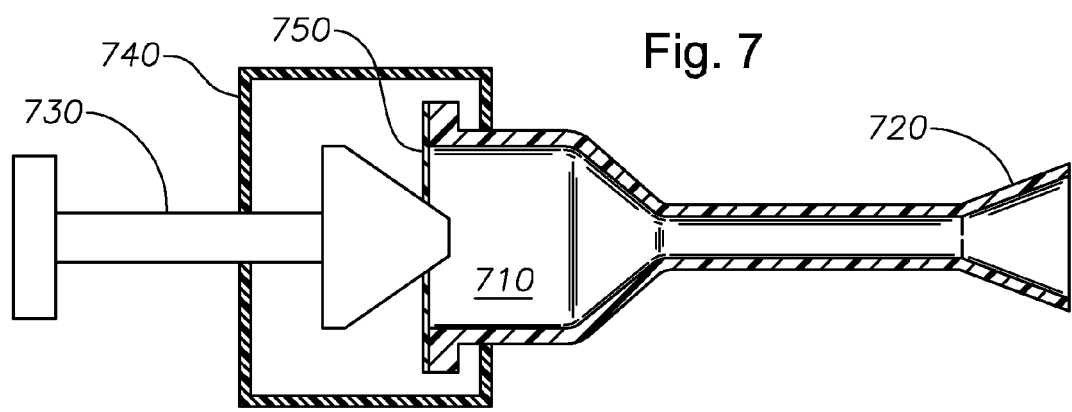
FIG. 7 is a cross section view of a fan-shaped cannula incision sealing device with a plunger according to the principles of the present invention.

FIG. 7 is a cross-section view of a fan-shaped cannula incision sealing device with a plunger according to the principles of the present invention. In the embodiment of FIG. 7, a syringe has been attached to the device of FIG. 4. The resulting device is ready for use to inject a sealant into an ophthalmic incision. The device includes chamber 710, fan-shaped cannula 720, plunger 730, plunger housing 740, and seal 750 (which has been pierced by plunger 730). In this embodiment, a standard syringe may be used. The fan-shaped cannula incision sealing device is attached to one end of the syringe. The plunger (or other structure such as the mounting hub of the syringe) pierces seal 750. Plunger 730 can then be depressed to push the sealant out of chamber 710, through fan-shaped cannula 720, and into (or onto) an incision. Plunger 730 and plunger housing 740 may be of any suitable configuration and may be implemented with a standard syringe of any suitable size. Likewise, a similar seal may be located at the tip end of fan-shaped cannula.

Figure 8:
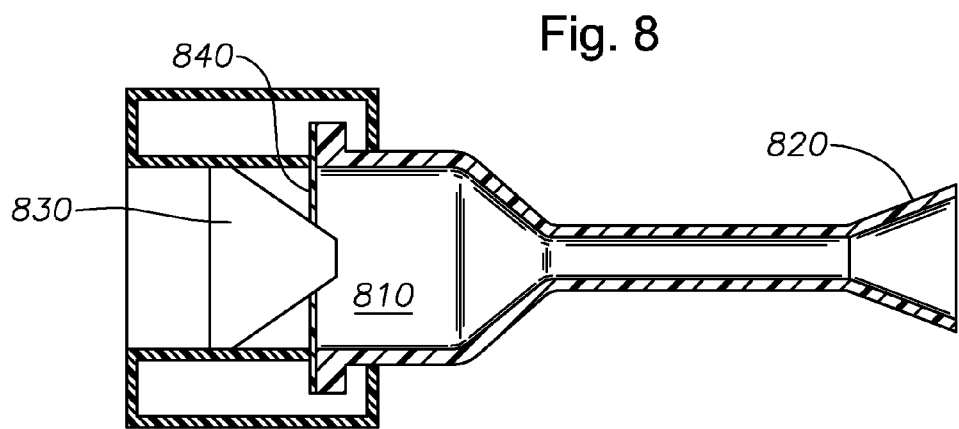
FIG. 8 is a cross section view of a fan-shaped cannula incision sealing device with a pneumatic plunger according to the principles of the present invention.

FIG. 8 is a cross-section view of a fan-shaped cannula incision sealing device with a pneumatic plunger according to the principles of the present invention. In the embodiment of FIG. 8, a pneumatic driver has been attached to the device of FIG. 4. The resulting device is ready for use to inject a sealant into an ophthalmic incision. The device includes chamber 810, fan-shaped cannula 820, plunger 830, and seal 840 (which has been pierced by plunger 830). In this embodiment, sealant may be pneumatically expelled from chamber 810, through cannula 820, and into (or onto) an incision. Force from a pneumatic pulse drives plunger 830 downward. Likewise, a similar seal may be located at the tip end of fan-shaped cannula.

Figure 9:
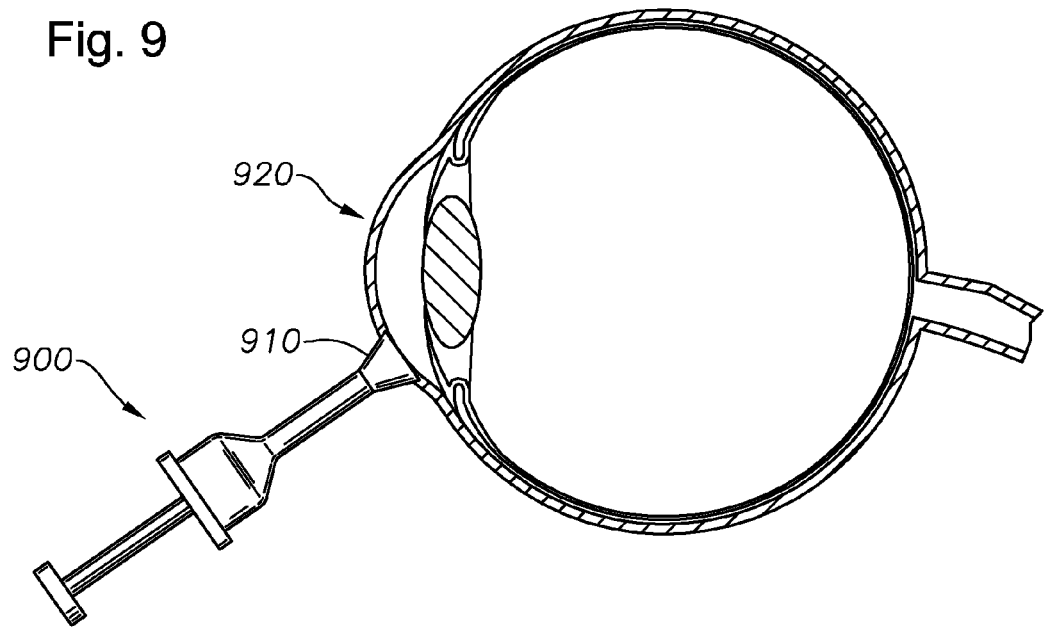
FIG. 9 is a cross section view of a fan-shaped cannula incision sealing device as used in an eye according to the principles of the present invention.

FIG. 9 is a cross section view of a fan-shaped cannula wound sealing device as used in an eye according to the principles of the present invention. In FIG. 9, fan-shaped cannula incision sealing device with a syringe 900 is being used to close an incision made during cataract surgery. An incision has been made in cornea 920. The end 910 of fan-shaped cannula has been inserted into this incision so that a sealant can be applied to seal the incision. While a cataract incision is depicted, any other type of incision made during ophthalmic procedures can be sealed in a like manner. For example, a scleral incision may be sealed using a fan-shaped cannula incision sealing device.

Figure 10:
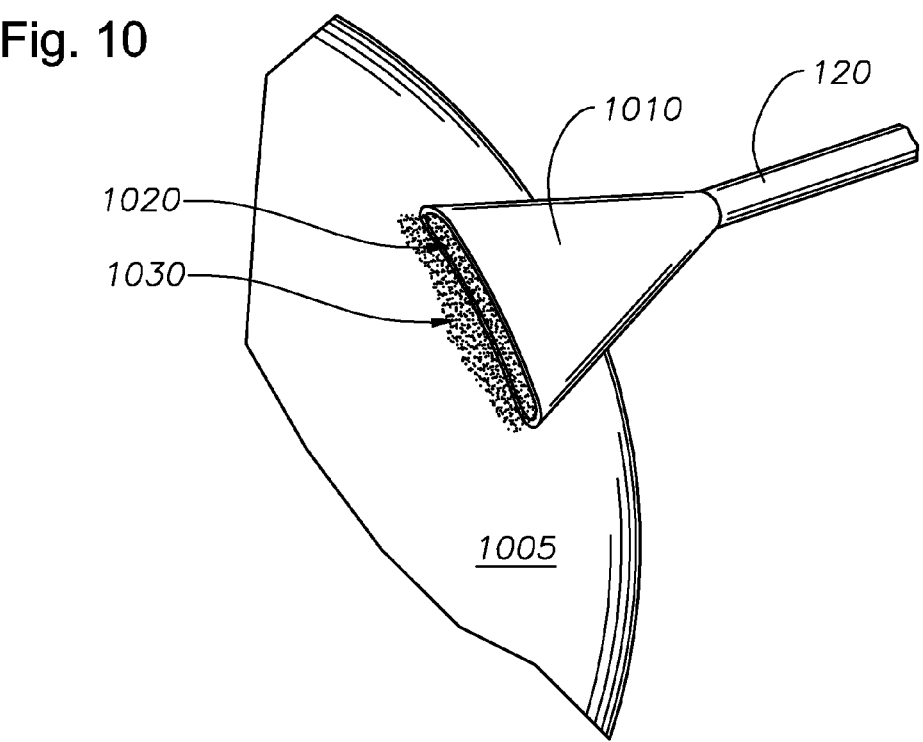
FIG. 10 is a perspective view of a fan-shaped cannula as used on an eye according to the principles of the present invention.

FIG. 10 is a perspective view of a fan-shaped cannula as used on an eye according to the principles of the present invention. In FIG. 10, a fan shaped cannula is configured to apply a sealant to an incision in an eye 1005. Sealant 1030 may be applied to the surface of eye 1005 at the incision site, or it may be applied to the incision itself. In FIG. 10, the fan-shaped tip extends along surface 1010 from cannula 120 to tip opening 1020. Sealant 1030 exits tip opening 1020 and is applied to the incision. In this embodiment, a fan-shaped tip with a curved profile (like that depicted in FIG. 2B or 2C) is used. The curvature of the fan-shaped tip (curvature of surface 1010 and the surface opposite surface 1010) helps the fan-shaped tip to conform to the generally spherical surface of the eye 1005.

From the above, it may be appreciated that the present invention provides an improved system for sealing incisions made during ophthalmic procedures. The present invention provides a fan-shaped cannula incision sealing device that dispenses an adhesive, epoxy, glue, sealant, or the like to close an incision. The tip end of the fan-shaped cannula and its opening are configured to properly dispense the sealant based on the incision geometry. The present invention is illustrated herein by example, and various modifications may be made by a person of ordinary skill in the art.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A device for delivering an incision sealant comprising:
   a housing at least partially enclosing a chamber, the chamber holding a quantity of an ophthalmic sealant;
   a seal located on one end of the housing, the seal containing the quantity of the sealant in the chamber; and
   a cannula fluidly coupled to the chamber, the cannula with a generally fan-shaped end, the generally fan-shaped end having a top and bottom surface and an original opening for dispensing the sealant;
   wherein the opening of the generally fan-shaped end is oblong;
   wherein the cannula with the generally fan-shaped end further comprises score marks delineating break points along the generally fan-shaped end for modifying the cannula by removing material past the break points;
   wherein when the generally fan-shaped end is broken along the score marks, a resulting opening has a different size than the original opening.

2. The device of claim 1 wherein the opening of the generally fan-shaped end has a curved edge and the top and bottom surfaces are curved.

3. The device of claim 1 wherein the top surface of the generally fan-shaped end is generally spoon-shaped.

4. The device of claim 1 wherein the generally fan-shaped end further comprises:
   a lip on the top surface of the generally fan-shaped end, the lip for scraping excess sealant from the incision.

5. The device of claim 1 wherein the cannula with the generally fan-shaped end is made of a polymer.

6. The device of claim 1, wherein when the generally fan-shaped end is broken along a score mark of the one or more score marks, a resulting opening has a different shape than the original opening.

7. The device of claim 1 further comprising:
   a plunger for breaking the seal and displacing the sealant from the chamber.

8. The device of claim 1 wherein the opening of the generally fan-shaped end generally lies along a curvilinear surface.

9. The device of claim 1, wherein the cannula is made of polyethylene or polypropylene and wherein the score marks have a depth allowing the cannula to be snapped at the score marks.

10. A device for delivering an incision sealant comprising:
    a housing at least partially enclosing a first chamber and a second chamber, the first chamber holding a quantity of a first part of an ophthalmic sealant, the second chamber holding a quantity of a second part of the ophthalmic sealant;
    a first seal located on one end of the housing and a second seal located opposite the first seal, the seals for containing the quantity of the first part of the sealant in the first chamber and for containing the quantity of the second part of the sealant in the second chamber; and
    a cannula fluidly coupled to the first and second chambers, the cannula with a generally fan-shaped end, the generally fan-shaped end having a top and bottom surface and an original opening for dispensing the sealant;
    wherein the opening of the generally fan-shaped end is oblong;
    wherein the cannula with the generally fan-shaped end further comprises score marks delineating break points along the generally fan-shaped end for modifying the cannula by removing material past the break points;
    wherein when the generally fan-shaped end is broken along the score marks, a resulting opening has a different size than the original opening.

11. The device of claim 10 wherein the opening of the generally fan-shaped end has a curved edge and the top and bottom surfaces are curved.

12. The device of claim 10 wherein the top surface of the generally fan-shaped end is generally spoon-shaped.

13. The device of claim 10 wherein the generally fan-shaped end further comprises:
    a lip on the top surface of the generally fan-shaped end, the lip for scraping excess sealant from the incision.

14. The device of claim 10 further comprising:
    a plunger for breaking the seal and displacing the sealant from the chamber.

15. The device of claim 14 further comprising:
    a source of pneumatic power for moving the plunger.

16. The device of claim 10 wherein the opening of the generally fan-shaped end generally lies along a curvilinear surface.

17. The device of claim 10, wherein when the generally fan-shaped end is broken along the score marks, a resulting opening has a different shape than the original opening.

18. The device of claim 10, wherein the cannula is made of polyethylene or polypropylene and wherein the score marks have a depth allowing the cannula to be snapped at the score marks.

* * * * *